US010709517B2

(12) United States Patent
Berkelaar

(10) Patent No.: US 10,709,517 B2
(45) Date of Patent: Jul. 14, 2020

(54) END EFFECTOR

(71) Applicant: Multi Scopic Instruments, LLC, Norwell, MA (US)

(72) Inventor: Gerald J. Berkelaar, Norwell, MA (US)

(73) Assignee: Multi Scopic Instruments, LLC, Norwell, MA (US)

( * ) Notice: Subject to any disclaimer, the term of this patent is extended or adjusted under 35 U.S.C. 154(b) by 279 days.

(21) Appl. No.: 15/872,288

(22) Filed: Jan. 16, 2018

(65) Prior Publication Data

US 2019/0216564 A1    Jul. 18, 2019

(51) Int. Cl.
| | | |
|---|---|---|
| *A61B 18/14* | (2006.01) | |
| *A61B 34/00* | (2016.01) | |
| *A61B 17/29* | (2006.01) | |
| *A61B 18/00* | (2006.01) | |
| *A61B 17/221* | (2006.01) | |
| *A61B 17/00* | (2006.01) | |

(52) U.S. Cl.
CPC .......... *A61B 34/71* (2016.02); *A61B 18/1445* (2013.01); *A61B 2017/00398* (2013.01); *A61B 2017/2212* (2013.01); *A61B 2017/2927* (2013.01); *A61B 2017/2936* (2013.01); *A61B 2017/2939* (2013.01); *A61B 2018/00595* (2013.01); *A61B 2018/146* (2013.01)

(58) Field of Classification Search
CPC ...... A61B 18/1445; A61B 2017/00398; A61B 2017/2212; A61B 2017/2927; A61B 2017/2936; A61B 2017/2939; A61B 2018/00595; A61B 2018/146; A61B 34/71

See application file for complete search history.

(56) References Cited

U.S. PATENT DOCUMENTS

| | | | |
|---|---|---|---|
| 4,880,015 A | * | 11/1989 | Nierman ................ A61B 10/06 600/564 |
| 5,133,727 A | | 7/1992 | Bales et al. |
| 5,209,747 A | | 5/1993 | Knoepfler |
| 5,314,445 A | * | 5/1994 | Heidmueller nee Degwitz .......... A61B 17/320016 606/174 |
| 5,345,831 A | | 9/1994 | Sandrock |
| 5,389,098 A | | 2/1995 | Tsuruta et al. |
| 5,395,369 A | | 3/1995 | McBrayer et al. |
| 5,447,513 A | | 9/1995 | Davison et al. |

(Continued)

FOREIGN PATENT DOCUMENTS

CA    2982615    3/2018

OTHER PUBLICATIONS

International Searching Authority/US, International Search Report and Written Opinion of the International Searching Authority, Application No. PCT/US2019/013632, dated Apr. 8, 2019, 11 pages.

*Primary Examiner* — Michael F Peffley
(74) *Attorney, Agent, or Firm* — Sunstein LLP

(57) ABSTRACT

An end effector has three degrees of freedom in operation: (1) opening and closing of the jaws, (2) adjustable articulation of the jaw plane relative to the longitudinal axis, and (3) rotation of the jaw assembly, regardless of its articulation, about the longitudinal axis. A split yoke assembly is coupled to rotatable jaw mounts, which in turn are coupled to the jaws. A pushrod is configured to open and close the jaws, and cables coupled to the rotatable jaw mounts cause articulation of the jaw plane.

10 Claims, 17 Drawing Sheets

(56) References Cited

U.S. PATENT DOCUMENTS

| | | |
|---|---|---|
| 5,454,827 A | 10/1995 | Aust et al. |
| 5,490,819 A | 2/1996 | Nicholas et al. |
| 5,578,052 A | 11/1996 | Koros et al. |
| 5,582,615 A | 12/1996 | Foshee et al. |
| 5,762,067 A | 6/1998 | Dunham et al. |
| 5,782,749 A | 7/1998 | Riza |
| 5,846,240 A | 12/1998 | Kortenbach et al. |
| 5,860,995 A * | 1/1999 | Berkelaar .............. A61B 17/29 606/174 |
| 6,506,208 B2 | 1/2003 | Hunt et al. |
| 6,663,640 B2 | 12/2003 | Kortenbach |
| 7,087,071 B2 | 8/2006 | Nicholas et al. |
| 7,147,650 B2 | 12/2006 | Lee |
| 7,322,935 B2 | 1/2008 | Palmer et al. |
| 7,678,117 B2 | 3/2010 | Hinman et al. |
| 7,927,327 B2 | 4/2011 | Lu et al. |
| 8,037,591 B2 | 10/2011 | Spivey et al. |
| 9,119,657 B2 | 9/2015 | Shelton, IV et al. |
| 9,629,688 B2 | 4/2017 | Robert et al. |
| 9,675,329 B2 | 6/2017 | Berkelaar |
| 9,925,014 B2 | 3/2018 | Robert et al. |
| 10,285,676 B2 | 5/2019 | Berkelaar |
| 2005/0090809 A1 | 4/2005 | Cooper et al. |
| 2006/0020287 A1 | 1/2006 | Lee et al. |
| 2007/0162072 A1 | 7/2007 | Nicholas et al. |
| 2008/0077159 A1 | 3/2008 | Madhani et al. |
| 2008/0287741 A1 | 11/2008 | Ostrovsky et al. |
| 2009/0062814 A1 | 3/2009 | Omori et al. |
| 2009/0171147 A1 | 7/2009 | Lee et al. |
| 2010/0168722 A1 | 7/2010 | Lee et al. |
| 2014/0249574 A1 | 9/2014 | Piskun et al. |
| 2017/0105746 A1 | 4/2017 | O'Keefe et al. |
| 2018/0193086 A1 | 7/2018 | Robert et al. |
| 2019/0133596 A1* | 5/2019 | Brodaczewski ... A61B 17/1285 |
| 2019/0209172 A1* | 7/2019 | Shelton, IV ..... A61B 17/00234 |
| 2019/0336157 A1* | 11/2019 | Ahrens ............. A61B 17/1606 |

* cited by examiner

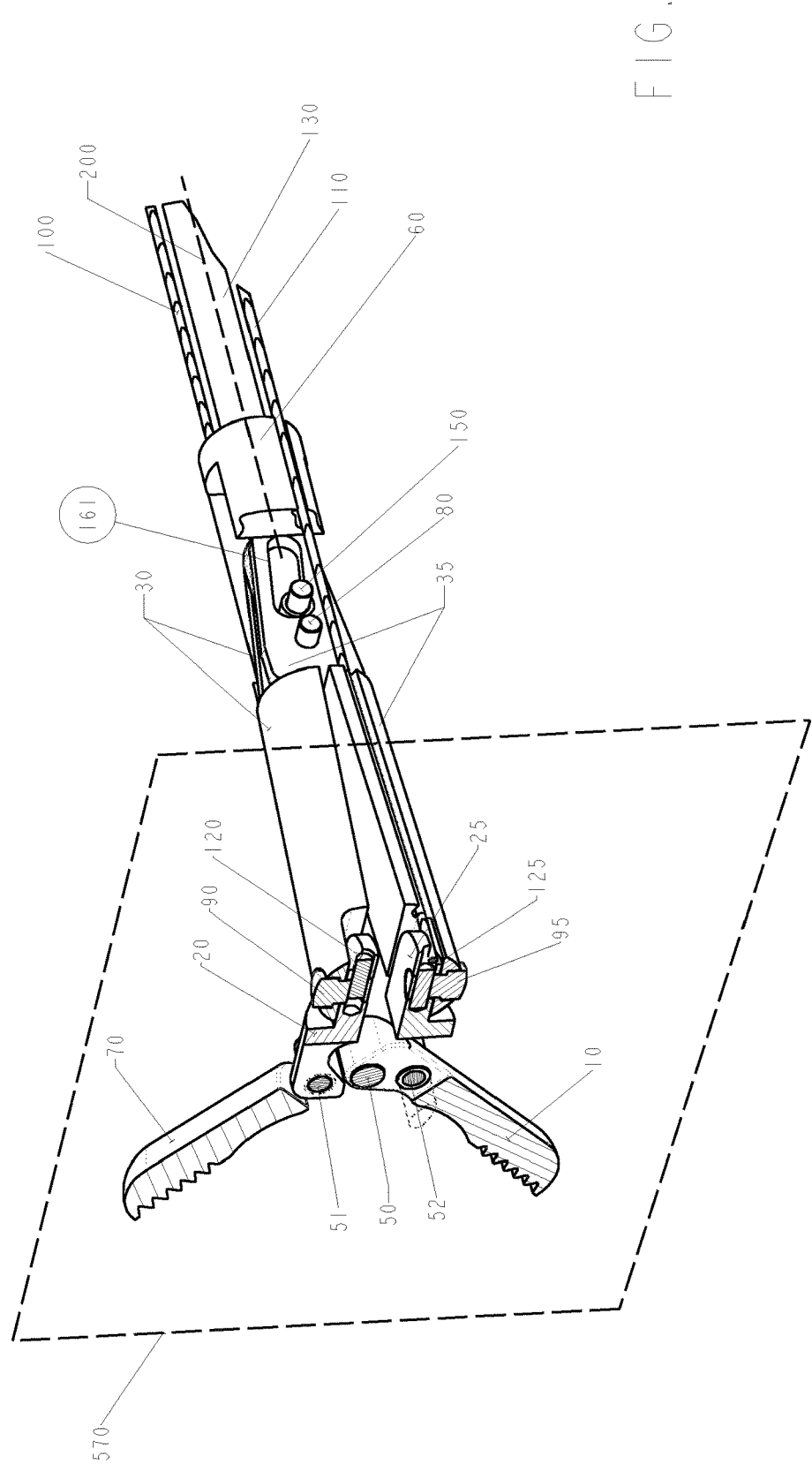

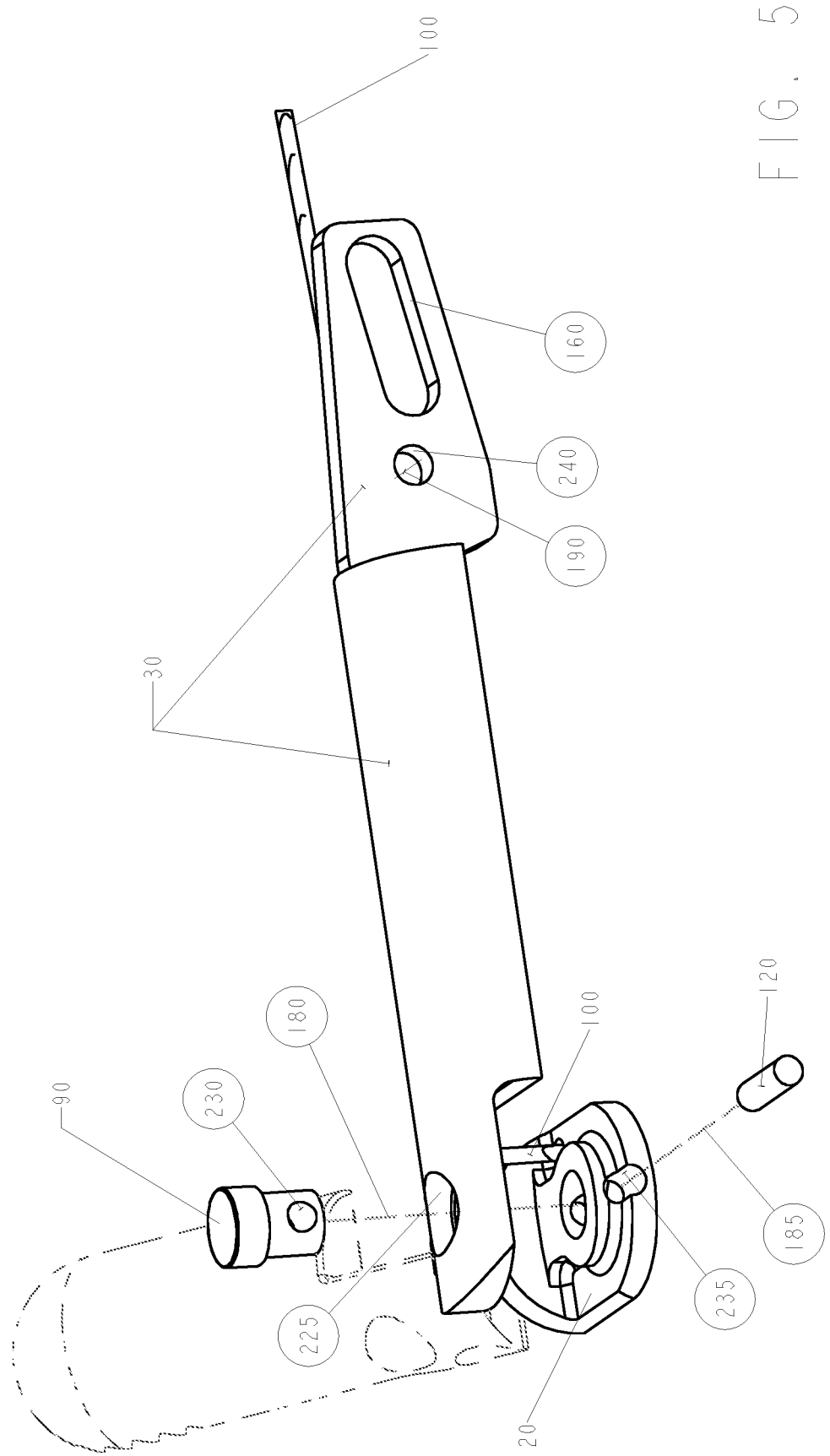

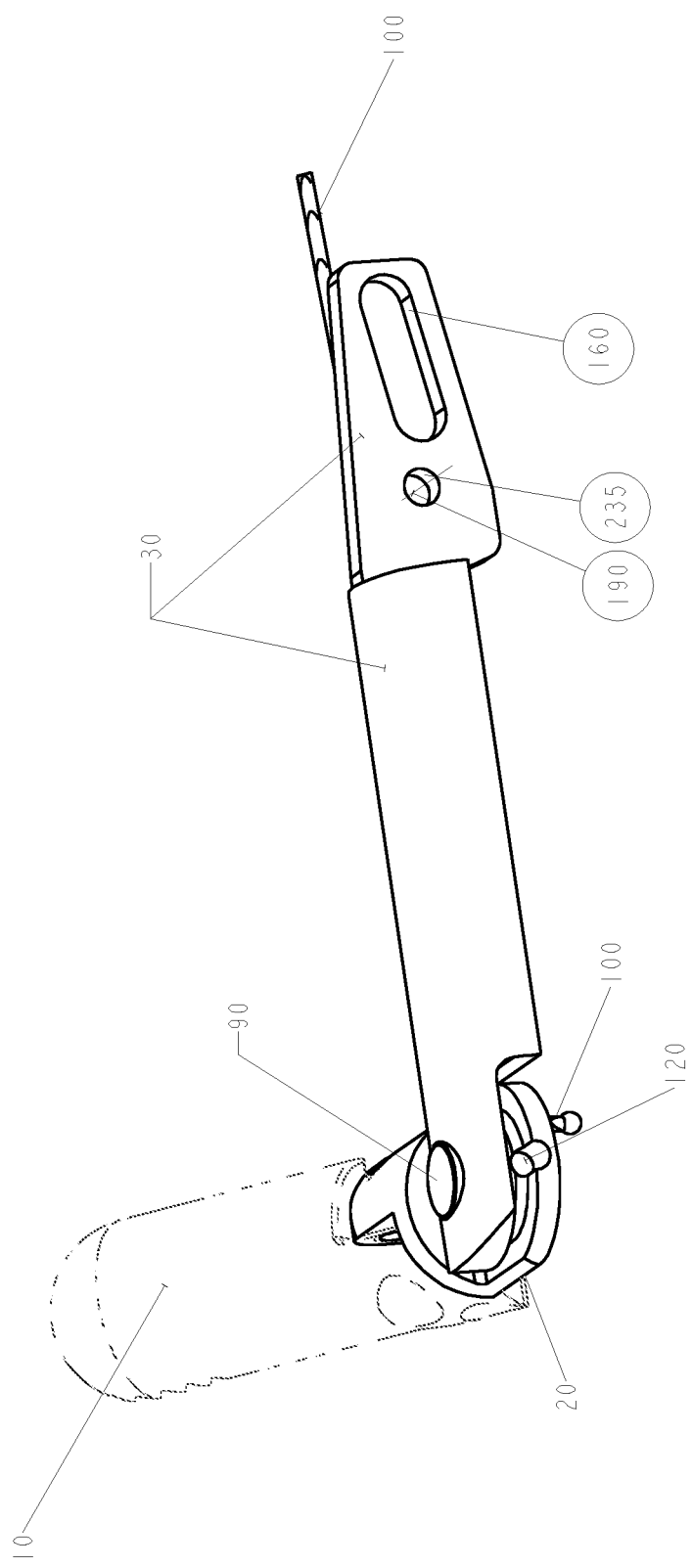

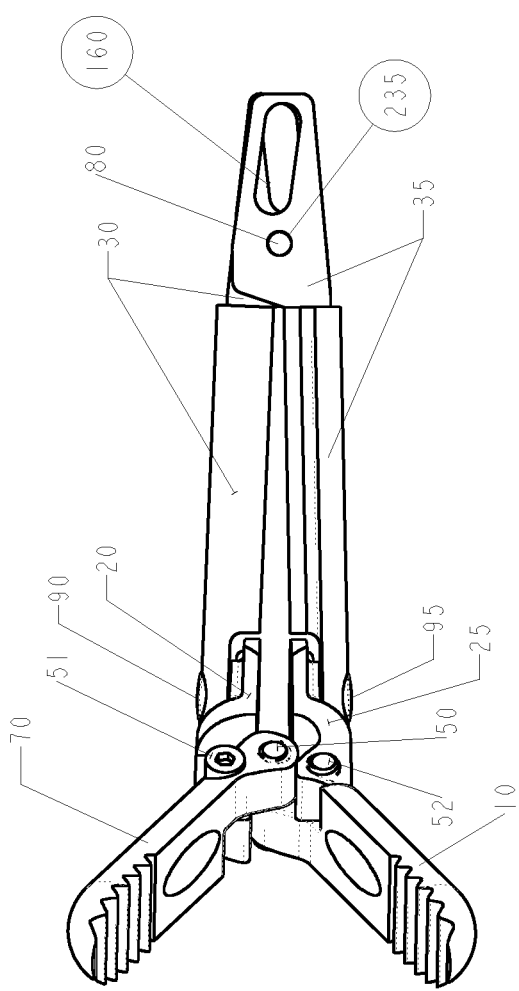
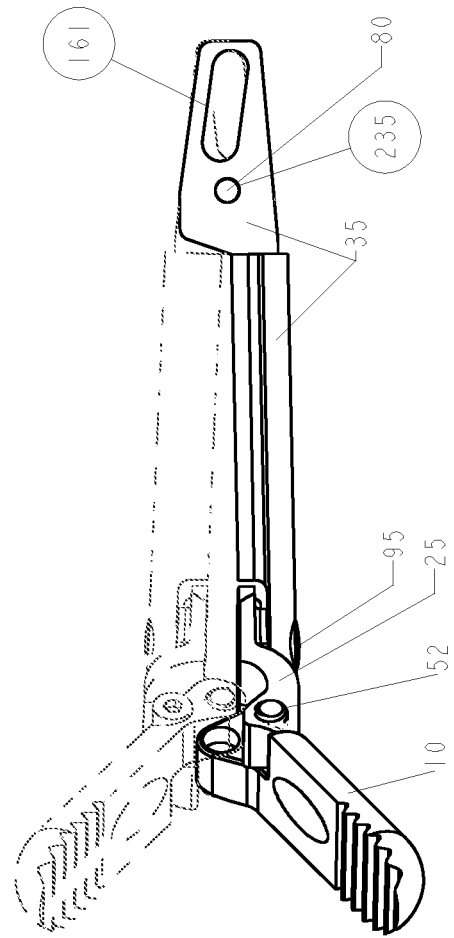
FIG. 7A
FIG. 7B

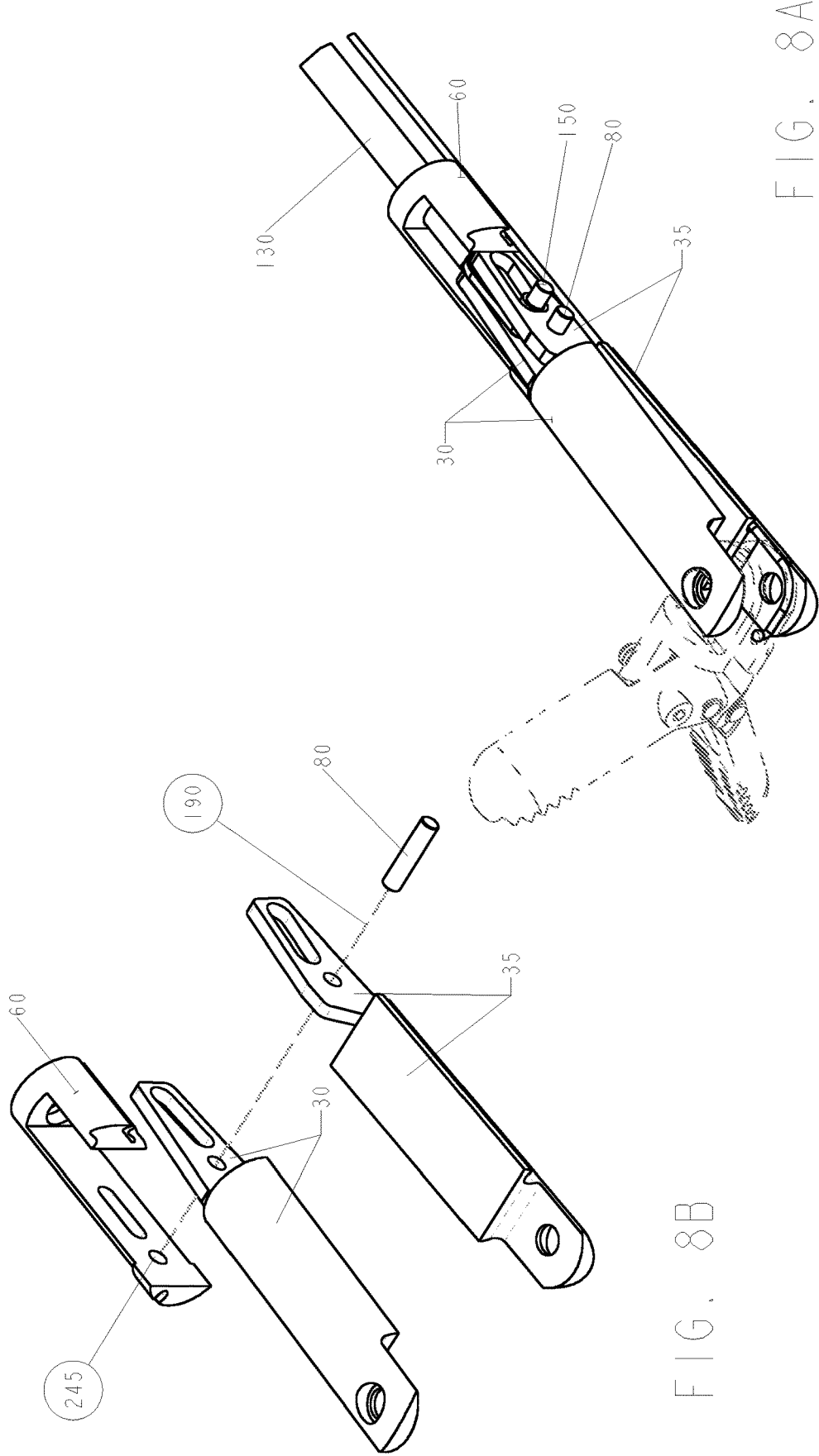

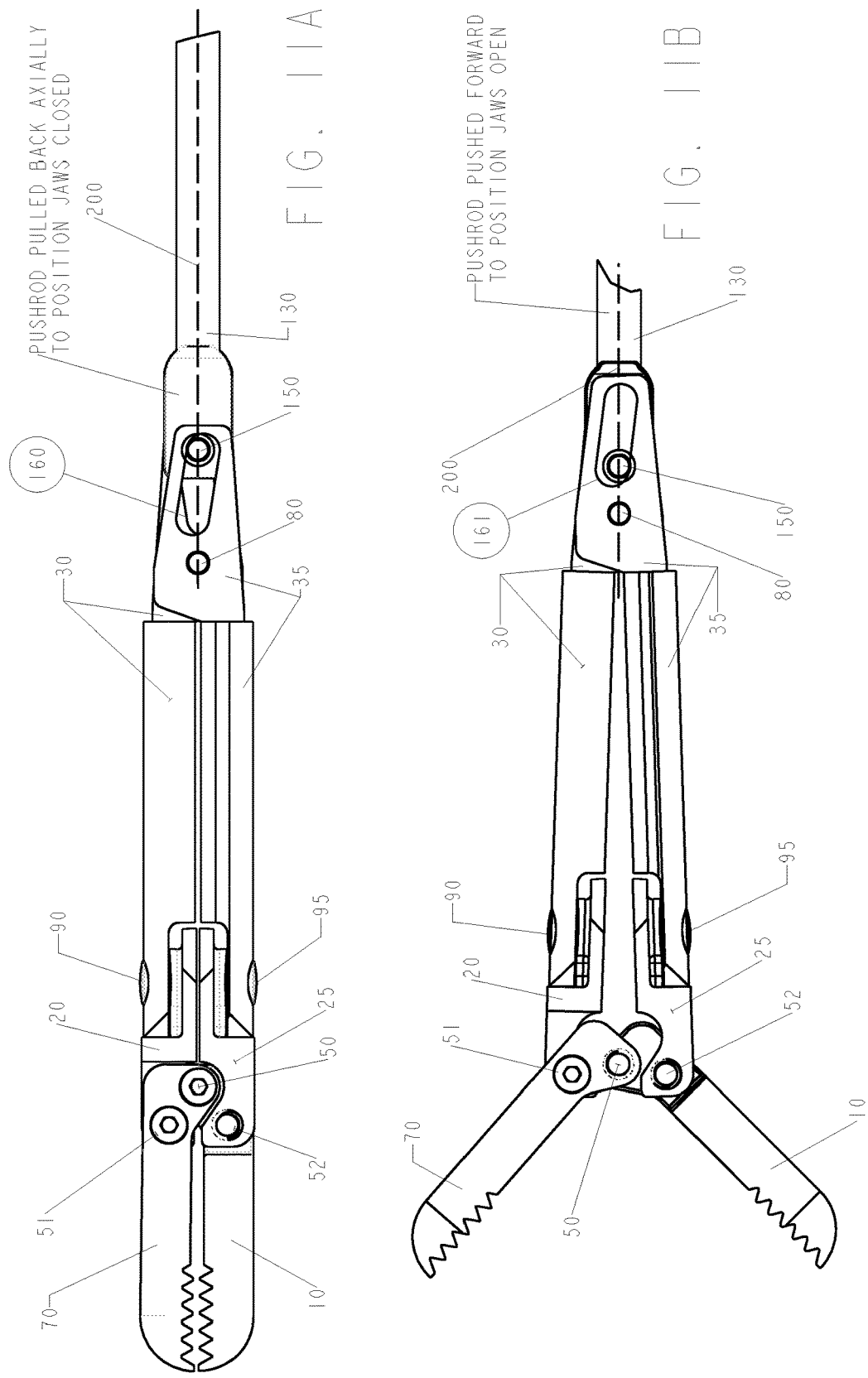

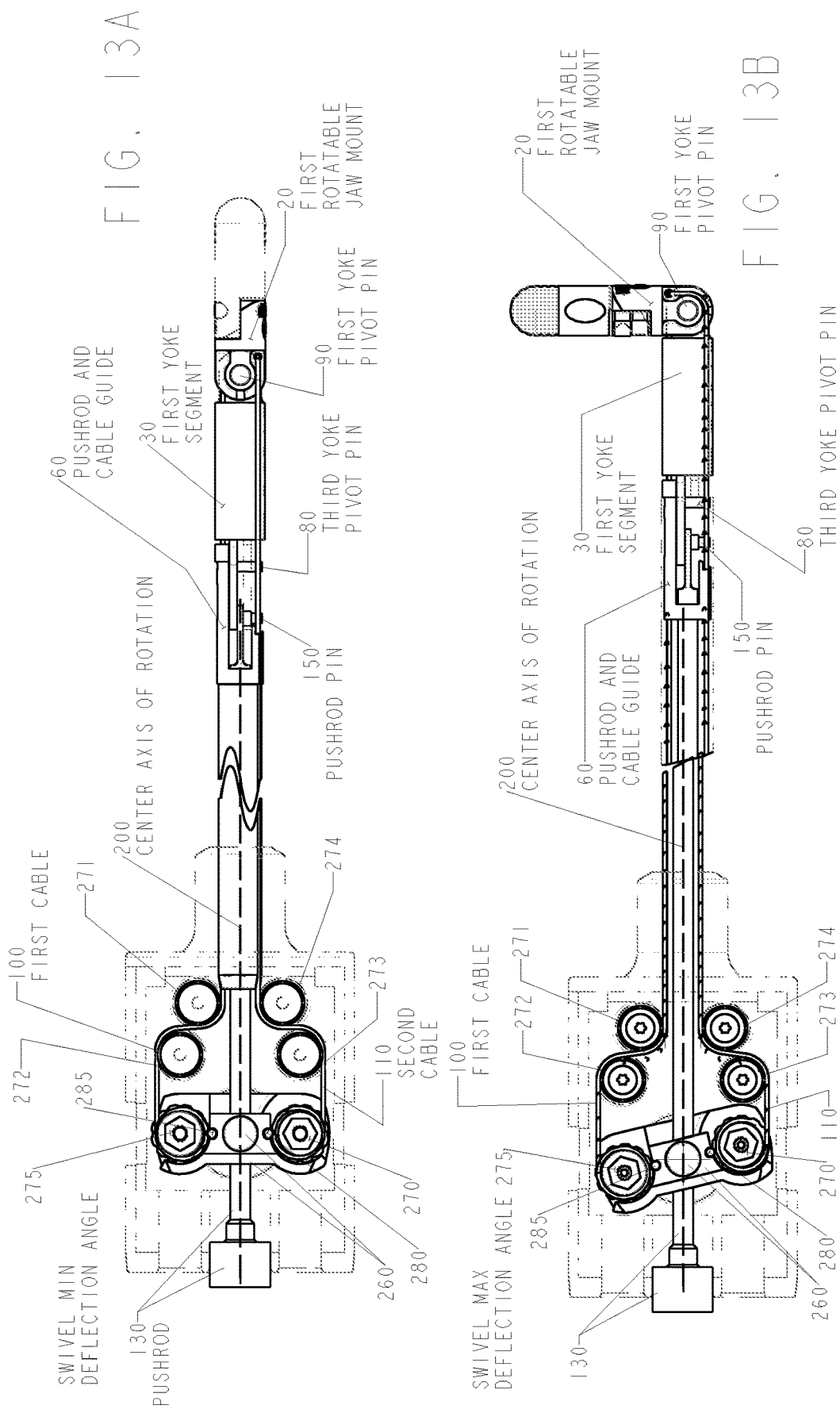

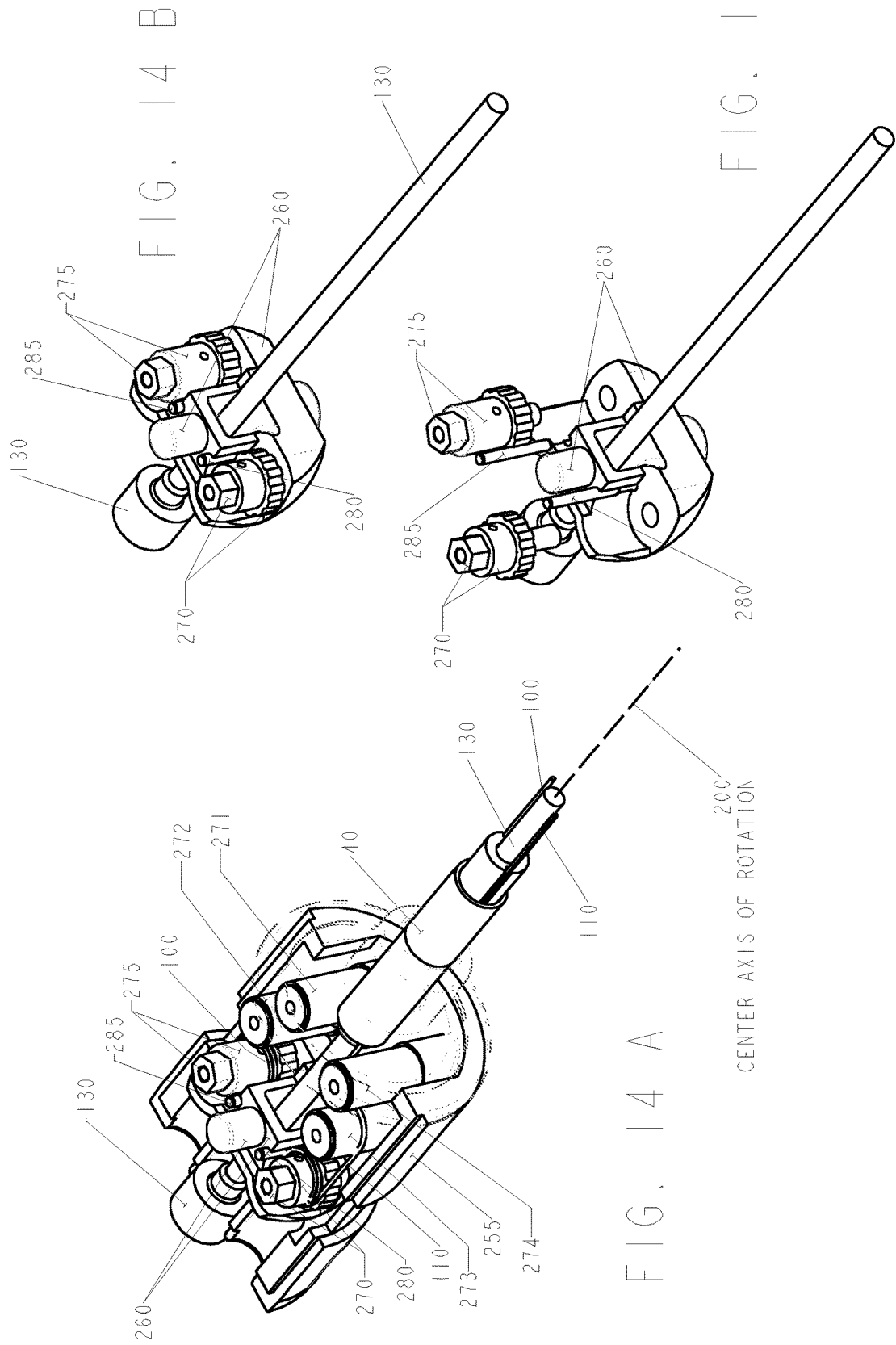

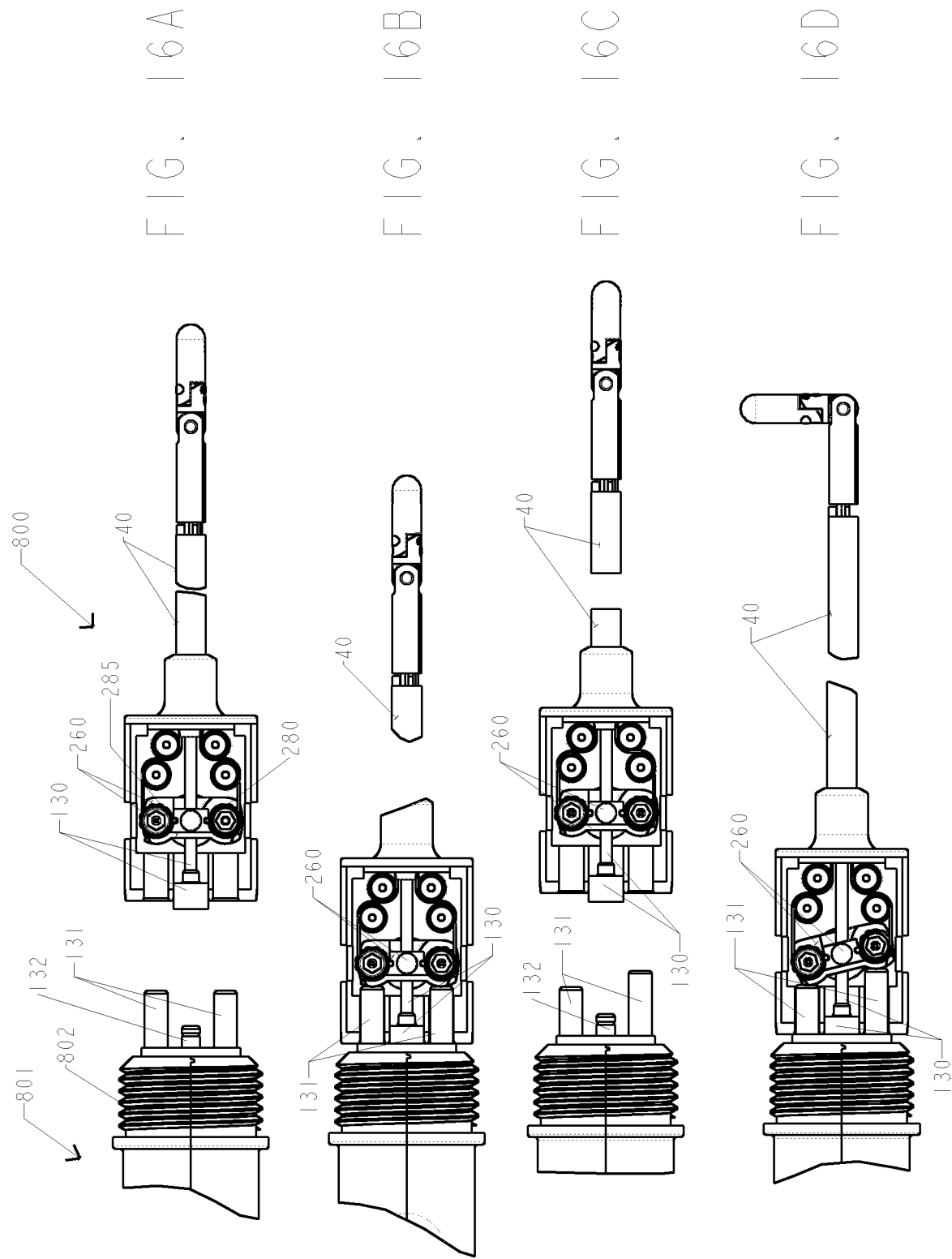

END EFFECTOR

TECHNICAL FIELD

The present invention relates to end effectors, and more particularly to grasping devices for medical and other applications.

BACKGROUND ART

End effectors are known in the prior art, including manually operated grasping devices and grasping devices for powered operation. Representative prior art devices are disclosed in U.S. Pat. No. 5,209,747, disclosing a rotatable arm having a jaw element; U.S. Pat. No. 7,087,071, disclosing an articulated endoscopic surgical apparatus; and U.S. Pat. No. 8,037,591, disclosing a surgical scissors.

SUMMARY OF THE EMBODIMENTS

In accordance with one embodiment of the invention, there is provided an end effector comprising:
an outer sleeve defining a central longitudinal axis;
first and second jaws;
a jaw pivot, mounted in each of the jaws, rotatably coupling the jaws and defining a jaw axis about which rotation of the jaws achieves opening and closing of the jaws, wherein (i) the jaw axis defines a jaw plane perpendicular thereto in which the jaws move relative to one another and (ii) the coupled jaws form a jaw assembly;
a split yoke assembly, generally aligned with the longitudinal axis, having first and second yoke segments, each yoke segment having a distal end and a proximal end, the yoke segments being mounted, about a scissors pivot, for scissors-movement with respect to one another;
a set of first and second rotatable jaw mounts, each jaw mount having proximal and distal ends, the distal end of each rotatable jaw mount being pivotally mounted, via a corresponding jaw mount pivot, to a corresponding one of the first and second jaws, and, the proximal ends of the first and second rotatable jaw mounts being pivotally mounted, via first and second yoke pivots, respectively, to the distal ends of the corresponding first and second yoke segments, wherein the jaw mount pivots define axes of rotation that are parallel to the jaw axis, to support opening and closing of the jaws in the jaw plane, and the first and second yoke pivots define first and second yoke pivot axes respectively and collectively configure rotation of the jaw assembly relative to longitudinal axis so that, in a straight-ahead position of the jaw assembly about the jaw mount pivots, the jaw plane is aligned with the longitudinal axis, and in an angled position of the jaw assembly about the jaw mount pivots, the jaw plane is at an angle to the longitudinal axis;
first and second cables coupled at a distal end thereof to the set of rotatable jaw mounts and at a proximal end thereof to a jaw-positioning assembly configured to move the position of the jaw assembly between the straight-ahead position and the angled position;
a pushrod having proximal and distal ends, the pushrod being mounted in the outer sleeve for axial motion along the longitudinal axis between a forward position in a direction toward the jaw assembly and a rearward position in a direction away from the jaw assembly;
a linkage system, coupled (a) to the first and second yoke segments near the proximal ends thereof and (b) to the distal end of the pushrod, the linkage system configured to move the proximal ends of the yoke segments towards each other, and therefore the distal ends of the yoke segments away from each other, so as to cause the jaws to move into an open position, when the pushrod is in a first one of the forward and rearward positions, and to move the proximal ends of the yoke segments away from each other, and therefore the distal ends of the yoke segments toward each other, so as to cause the jaws to move into a closed position, when the pushrod is in a second one of the forward and rearward positions.

In a further related embodiment, the proximal ends of the yoke segments have facing flattened surfaces that are approximately in the jaw plane when the jaw assembly is in the straight-ahead position, and the linkage system includes:
a set of angled slots formed in the proximal ends of the yoke segments,
a yoke segment positioning system disposed around the proximal ends of the yoke segments and coupled to the outer sheath, and
a positioning pin, mounted in the positioning system at right angles to the flattened surfaces of the proximal ends of the yoke segments, and located within the slots of both of the yoke segments, and the pushrod is coupled to the positioning pin, so that axial motion of the pushrod causes the positioning pin in combination with the angled slots to move the proximal ends of the yoke segments towards or away from each other, depending on the direction of the axial motion.

In yet another related embodiment, the jaws are configured for grasping.

In yet another related embodiment, the jaws are configured as scissor blades for cutting.

In yet another related embodiment, the jaws are configured to carry current to enable use thereof in electrocautery.

BRIEF DESCRIPTION OF THE DRAWINGS

The foregoing features of embodiments will be more readily understood by reference to the following detailed description, taken with reference to the accompanying drawings, in which:

FIG. 1B is a perspective view similar to that of FIG. 1A, but showing, however, a section taken through the jaw plane 570;

FIG. 5 is an exploded perspective view of components of FIG. 1A including the first yoke segment 30 and first rotatable jaw mount 20;

FIG. 6 is an assembled perspective view of the components of FIG. 5;

FIG. 7A is an assembled perspective view of components of FIG. 1A including the jaw assembly, the first and second rotatable jaw mounts 20 and 25, and the first and second yoke segments 30 and 35;

FIG. 7B is an assembled perspective view of the components of FIG. 7A, but with the first jaw 10, the first rotatable jaw mount 20, and the first yoke segment 30 shown in phantom;

FIG. 8A is an assembled perspective view of components of FIG. 1A (with the outer sleeve 40 removed for purposes of illustration) including the first and second yoke segments 30 and 35, the scissors pivot 80, the positioning pin 150, and the yoke segment positioning system 60 (shown partially cut away);

FIG. 8B is an exploded perspective view of the components of FIG. 8A, with positioning system 60 shown partially cut away;

FIG. 11A is an assembled perspective view of components of FIG. 1A showing the first and second jaws 70 and 10 of the jaw assembly in a closed position (and aligned with the longitudinal axis 200 of the device) with first and second yoke segments 30 and 35 (with the outer sleeve 40 removed) and the positioning pin 150 in the rearward position as a result of rearward motion of the pushrod 130;

FIG. 11B is an assembled perspective view of components of FIG. 1A showing the first and second jaws 70 and 10 of the jaw assembly in an open position (and aligned with the longitudinal axis 200 of the device) with first and second yoke segments 30 and 35 (with the outer sleeve 40 removed) and the positioning pin 150 in the forward position as a result of forward motion of the pushrod 130;

FIG. 13A is a top view of an embodiment of the present invention including components of FIG. 1A as well as the proximal end of the device showing a housing in phantom and a spooling system for cables 100 and 110, in this view with the jaws closed and aligned with the longitudinal axis;

FIG. 13B is a top view of the embodiment of FIG. 13A, in this view with the jaws closed and articulated at approximately a right angle to the longitudinal axis;

FIG. 14A is a perspective view of the proximal end of the embodiment of FIGS. 13A and 13B, with the upper portion of the housing removed;

FIG. 14B is a similar perspective view of the embodiment of FIG. 14A, showing the mounting system for the proximal end of the pushrod removed from the housing;

FIG. 14C is a view similar to that of FIG. 14B, but with capstan assemblies 270 and 275 exploded from their seated positions;

FIGS. 16A, 16B, 16C, and 16D are top views of the end effector of FIG. 1A showing the entire disposable portion 800 of the instrument in relation to a portion 801 of the case, to which the disposable portion is removably attachable.

In FIG. 16A, the axis rotation drivers 131 are in a neutral position and detached from the disposable portion 800, and the end effectors face straight along the longitudinal axis 200.

In FIG. 16B, the axis rotation drivers 131 are engaged into the disposable portion 800 and in contact with swivel assembly 260.

In FIG. 16C, the axis rotation drivers 131 are in a maximum deflected position and detached from the disposable portion 800. The end effectors are aligned with the longitudinal axis 200. The swivel assembly 260 is in rest condition prior to the engagement of the case 801 with the disposable portion 800.

In FIG. 16D, after the case 801 is engaged with the disposable portion 800, the swivel assembly 260 is forced into an angled position by the axis rotation drivers 131 to cause the jaw plane to lie at right angles to the longitudinal axis.

DETAILED DESCRIPTION OF SPECIFIC EMBODIMENTS

Definitions. As used in this description and the accompanying claims, the following terms shall have the meanings indicated, unless the context otherwise requires:

A "set" includes at least one member.

A "jaw assembly" of first and second jaws, rotatably coupled by a jaw pivot defining a jaw axis about which rotation of the jaws achieves opening and closing of the jaws, includes (i) grasping embodiments wherein the jaws are equipped with surfaces that come into contact with one another when the jaws are closed and the jaws are configured for grasping objects, (ii) cutting embodiments wherein the jaws are embodied as scissor blades and configured as scissors for performing cutting operations, and (iii) other manipulation embodiments wherein the jaws operate items such as loops or prods.

A "linkage system" is an assembly of mechanical bodies coupled to manage forces and movement and is not limited to a system of pivoted links.

A "proximal end" of a device or component thereof having proximal and distal ends is the end of the device or component that when in use is closer to the user.

A "distal end" of a device or component thereof having proximal and distal ends is the end of the device or component that when in use is farther from the user.

Figure 1A:
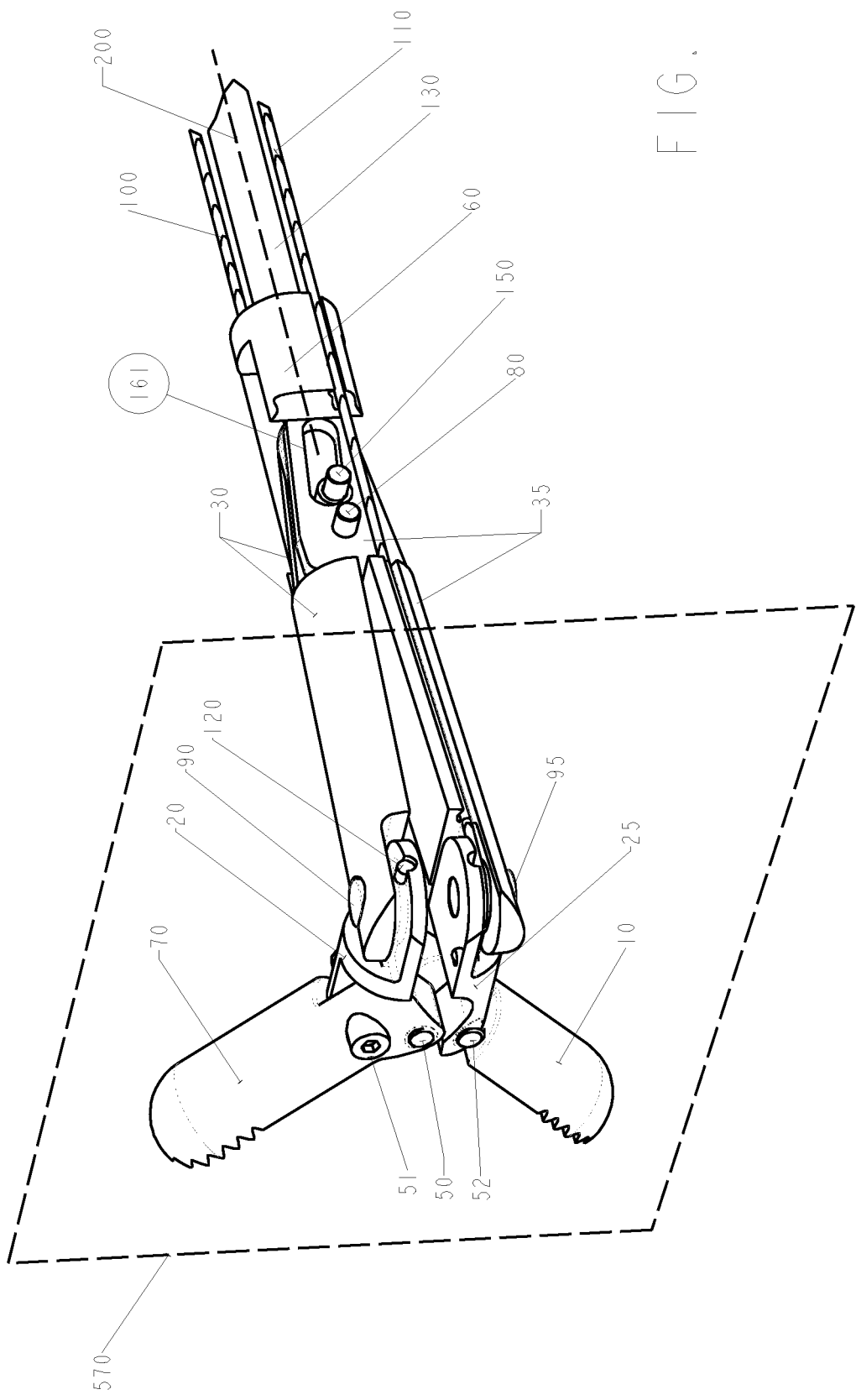
FIG. 1A is a perspective view of a distal end of a device, in accordance with an embodiment of the present invention, with the outer sleeve 40 removed for purposes of illustration.

FIG. 1A is a perspective view of a distal end of a device, in accordance with an embodiment of the present invention, with the outer sleeve 40 removed for purposes of illustration. FIG. 1B is a perspective view similar to that of FIG. 1A, but showing, however, a section taken through the jaw plane 570. The device has first jaw 70 and second jaw 10 rotatably coupled by a jaw pivot screw 50, defining a jaw axis about which rotation of the jaws achieves opening and closing of the jaws. The jaws, thus pivoted, form a jaw assembly, and the jaw axis defines a jaw plane 570 perpendicular thereto, in which the jaws move relative to one another so as to open and close. Relative motion of the jaws about the jaw pivot screw 50 is achieved using the pushrod 130 in the manner described below.

It is a feature in the embodiment of FIGS. 1A and 1B that the jaw assembly (and therefore the jaw plane 570) can be articulated with respect to the longitudinal axis 200 of the device, and, in FIG. 1B, the jaw plane 570 has been articulated to be at an angle of approximately 90 degrees with respect to the longitudinal axis 200. Articulation of the jaw plane 570 relative to the longitudinal axis 200 is achieved using first cable 100 and second cable 110 in a manner described below. In this embodiment, the pushrod 130 and other components are configured so as to open and close the jaws, regardless of the angle at with the jaw plane is articulated. Even when the jaw plane 570 is articulated to be at 90 degrees or more relative to the longitudinal axis, the pushrod 130 remains able to open and close the jaws. Moreover, as explained in further detail below, rotation of the outer sleeve 40 and the assembly 255 (see also FIG. 14A) to which it is attached has the effect of rotating the jaw assembly about the longitudinal axis. Consequently, the described embodiment provides three degrees of freedom in operation of the end effector: (1) opening and closing of the jaws, (2) adjustable articulation of the jaw plane relative to the longitudinal axis, and (3) rotation of the jaw assembly, regardless of its articulation, about the longitudinal axis.

The first and second jaws 70 and 10 respectively are mounted by first and second jaw mount pivot screws 51 and 52 respectively to distal ends of a set of first and second rotatable jaw mounts 20 and 25 respectively. The proximal ends of the first and second rotatable jaw mounts 20 and 25 are rotatably mounted, by first and second yoke pivot pins 90 and 95 respectively, to distal ends of first and second yoke segments 30 and 35 respectively of a split yoke assembly. The pivot pins 90 and 95 respectively in the first and second rotatable jaw mounts 20 and 25 respectively are secured respectively by first rocker pin 120 (shown in FIG. 1A) and a second rocker pin 121 (shown in FIG. 1B).

The jaw mount pivot screws 51 and 52 define axes of rotation that are parallel to the jaw axis, to support opening and closing of the jaws in the jaw plane 570. As the jaws open and close, with motion of each jaw about the jaw pivot screw 50, each jaw moves about its corresponding jaw mount pivot as necessary to accommodate opening and closing of the jaws. Additionally, the yoke pivot pins 90 and 95 define first and second yoke pivot axes respectively and collectively configure rotation of the jaw assembly relative to the longitudinal axis 200 so that, in a straight-ahead position of the jaw assembly about the jaw mount pivots, the jaw plane 570 is aligned with the longitudinal axis 200, and in an angled position of the jaw assembly about the jaw mount pivots, the jaw plane 570 is at an angle to the longitudinal axis 200.

The yoke assembly is split into first and second segments 30 and 35 to allow the distal ends of these segments to separate from one another when, as illustrated in FIGS. 1A and 1B, the jaws are in an open position. The amount of separation of the segments 30 and 35 increases when, as in FIGS. 1A and 1B, the pushrod 130 moves forward along the longitudinal axis 200.

The first and second yoke segments 30 and 35 are rotatably mounted about scissors pivot pin 80, so as to accommodate the separation and unification movement experienced by the distal ends of these yoke segments as the jaws open and close. In fact, it is the separation and unification movement of the distal ends of the yoke segments 30 and 35, about the scissors pivot pin 80, that effectuates the opening and closing respectively of the jaws 70 and 10. As described in further detail in connection with the figures below, the separation and unification of the distal ends of the yoke segments 30 and 35 are caused respectively by forward and rearward motion of the pushrod 130 respectively. In FIGS. 1A and 1B, the jaws are open, and the pushrod 130 is in the forward position.

As illustrated in further detail in FIG. 8B, each of the portions of the first and second yoke segments 30 and 35 that is located proximally with respect to the scissors pivot pin 80 includes a flattened face that contacts, or nearly contacts, the flattened face of the other such portion. The adjacent planes defined by the two flattened faces are located parallel and adjacent to the longitudinal axis 200. In each of the flattened faces of the proximal ends of first and second yoke segments 30 and 35 is an angled slot, and a positioning pin 150 is configured to protrude through both slots. Putting the pushrod 130 in the forward position causes the positioning pin 150 to be located in the forward position in the angled slots and causes separation of the distal ends of the yoke segments 30 and 35, and thus opening of the jaws, as further described below in connection with FIGS. 5, 6, 7A, 7B, 8A, 8B, 9, 10, 11A, and 11B.

FIG. 5 is an exploded perspective view of components of FIG. 1A including the first yoke segment 30 and first rotatable jaw mount 20. This figure shows the flattened proximal end of first yoke segment 30, containing angled slot 160 and hole 240 for scissors pivot pin 80. Also shown in FIG. 5 is the first yoke pivot pin 90, the first rocker pin 120, which secures the first yoke pivot pin 90 by insertion through hole 235 in the first rotatable jaw mount 20 and hole 230 in first yoke pivot pin 90 itself. Just barely visible is cable 100, at a location from which it emerges from the first rotatable jaw mount 20 and also in the upper right portion of the figure.

FIG. 6 is an assembled perspective view of the components of FIG. 5.

FIG. 7A is an assembled perspective view of components of FIG. 1A including the jaw assembly, the first and second rotatable jaw mounts 20 and 25, and the first and second yoke segments 30 and 35. Because, in this figure, the distal ends of the first and second yoke segments 30 and 35 are separated, their relative motion applies forces to the jaw assembly through the pivots 51 and 52 to cause the jaws 10 and 70 to open.

FIG. 7B is an assembled perspective view of the components of FIG. 7A, but with the first jaw 10, the first rotatable jaw mount 20, and the first yoke segment 30 shown in phantom. In this figure, the flattened proximal end of the second yoke segment 35 is readily apparent, with its angled slot 161. A comparison of the slot 161 in the second yoke segment 35 of this figure with the angled slot 160 in the flattened proximal end of the first yoke segment 30 of FIG. 6 shows that slot 160, as one traverses the yoke segment 30 from left to right, moves up vertically, whereas angled slot 161, as one traverses the yoke segment 35 from left to right, moves down vertically.

FIG. 8A is an assembled perspective view of components of FIG. 1A (with the outer sleeve 40 removed for purposes of illustration) including the first and second yoke segments 30 and 35, the scissors pivot pin 80, the positioning pin 150, and the yoke segment positioning system 60 (shown partially cut away). FIG. 8B is an exploded perspective view of these components of FIG. 8A. The proximal ends of the yoke segments 30 and 35 are disposed within the yoke segment positioning system 60. The positioning pin 150 passes through the yoke segment positioning system 60 in such a way as also to pass through both slots 160 and 161. Meanwhile a portion of the distal end of pushrod 130 entering the yoke segment positioning system 60 is flattened to lie between the faces of the proximal ends of the yoke segments 30 and 35 and to couple to the scissors pivot pin 80. Therefore forward motion of the pushrod 130 causes forward motion of the positioning pin 150 and angular rotation of the yoke segments 30 and 35 about the scissors pivot pin 80. Because, as explained in connection with FIGS. 6, 7A, and 7B, the angled slots 160 and 161 are oriented in opposed directions, as the proximal ends of the yoke segments 30 and 35 advance in the yoke segment positioning system 60, the positioning pin 150 has the effect of urging the proximal ends of the yoke segments 30 and 35 towards each other. Moreover, as these proximal ends are urged towards each other, the two yoke segments experience relative rotation about the scissors pivot pin 80 so as to cause the distal ends of the two yoke segments to experience separation, which, as explained above, causes the jaws of the jaw assembly to open.

Figure 9:
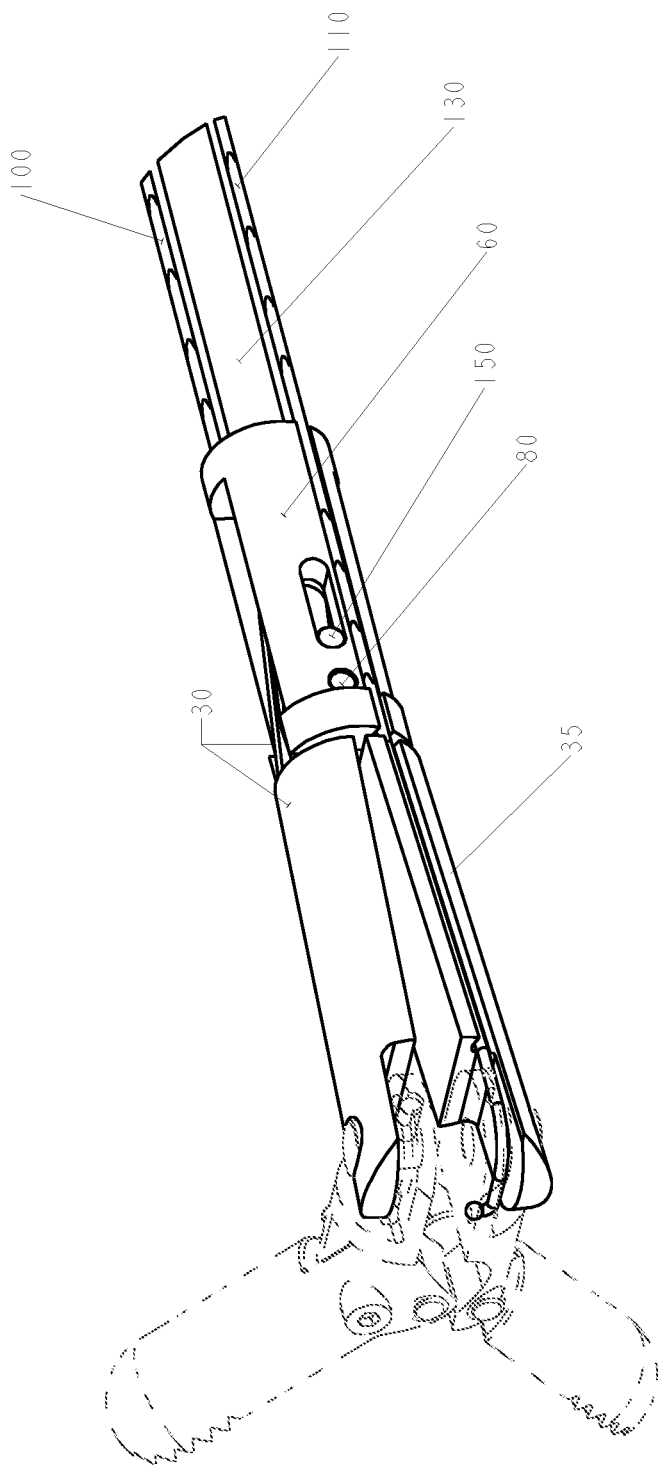
FIG. 9 is a further assembled perspective view of the components of FIG. 8A, but with the positioning system 60 shown intact and further showing the first and second cables 100 and 110 and the pushrod 130.

FIG. 9 is a further assembled perspective view of the components of FIG. 8A, but with the positioning system 60 shown intact and further showing the first and second cables 100 and 110 and the pushrod 130. Because, in FIGS. 8A and 9, the proximal ends of yoke segments 30 and 35 are in the forward position, the proximal ends are squeezed together and the distal ends are separated, so as to cause the jaws of the jaw assembly to be open.

Figure 10:
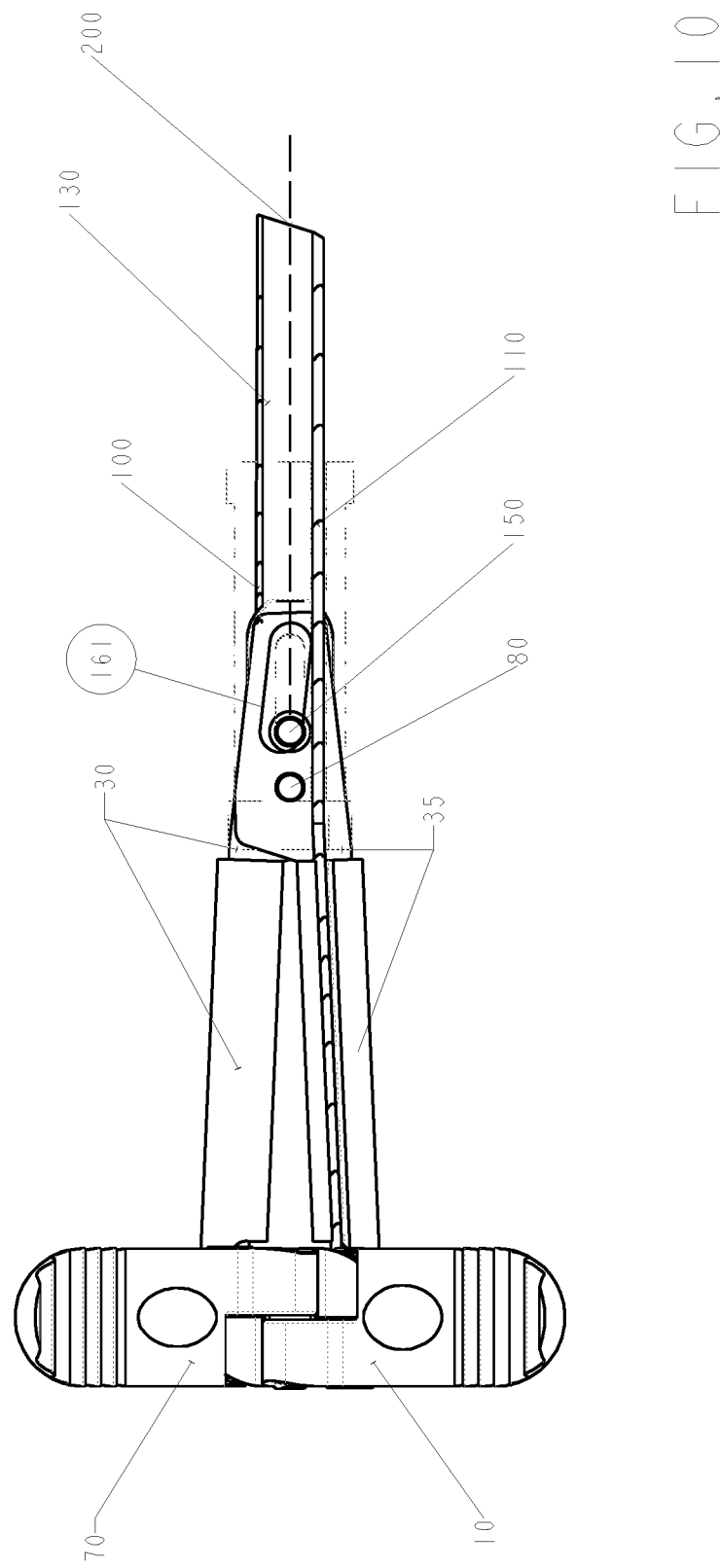
FIG. 10 is an assembled perspective view of components of FIG. 1A showing the first and second jaws 70 and 10 of the jaw assembly in an open position (and articulated at right angles to the longitudinal axis of the device) with first and second yoke segments 30 and 35 (with the outer sleeve 40 removed) and the positioning pin 150 in the forward position as a result of forward motion of the pushrod 130, and the positioning system shown in phantom.

FIG. 10 is an assembled perspective view of components of FIG. 1A showing the first and second jaws 70 and 10 of the jaw assembly in an open position (and articulated at right angles to the longitudinal axis of the device) with first and second yoke segments 30 and 35 (with the outer sleeve 40 removed and the yoke segment positioning system 60 shown in phantom) and the positioning pin 150 in the forward position as a result of forward motion of the pushrod 130.

FIG. 11A is an assembled perspective view of components of FIG. 1A showing the first and second jaws 70 and 10 of the jaw assembly in a closed position (and aligned with the longitudinal axis 200 of the device) with first and second yoke segments 30 and 35 (with the outer sleeve 40 removed) and the positioning pin 150 in the rearward position as a result of rearward motion of the pushrod 130.

FIG. 11B is an assembled perspective view of components of FIG. 1A showing the first and second jaws 70 and 10 of the jaw assembly in an open position (and aligned with the longitudinal axis 200 of the device) with first and second yoke segments 30 and 35 (with the outer sleeve 40 removed) and the positioning pin 150 in the forward position as a result of forward motion of the pushrod 130.

Figure 12C:
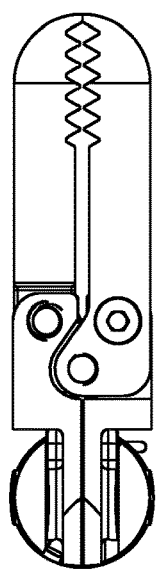
FIG. 12C is an end view of components of FIG. 1A, with the jaws 70 and 10 articulated at right angles to the longitudinal axis of the device, and in a closed position.
Figure 12B:
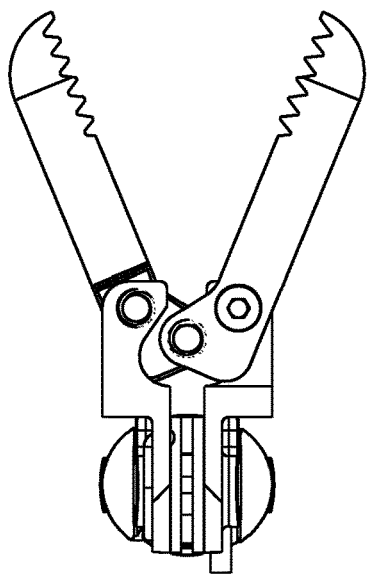
FIG. 12B is an end view of components of FIG. 1A, with the jaws 70 and 10 articulated at right angles to the longitudinal axis of the device, and in a partially open position.
Figure 12A:
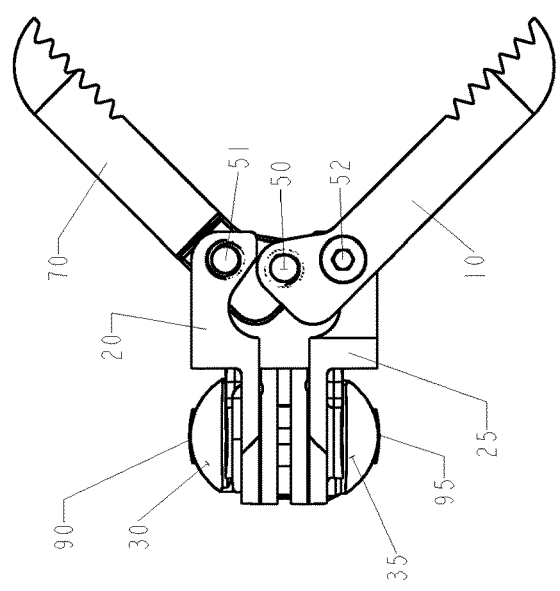
FIG. 12A is an end view of components of FIG. 1A, with the jaws 70 and 10 articulated at right angles to the longitudinal axis of the device, and in an open position.

FIG. 12A is an end view of components of FIG. 1A, with the jaws 70 and 10 articulated at right angles to the longitudinal axis of the device, and in an open position.

FIG. 12B is an end view of components of FIG. 1A, with the jaws 70 and 10 articulated at right angles to the longitudinal axis of the device, and in a partially open position.

FIG. 12C is an end view of components of FIG. 1A, with the jaws 70 and 10 articulated at right angles to the longitudinal axis of the device, and in a closed position.

Figure 2B:
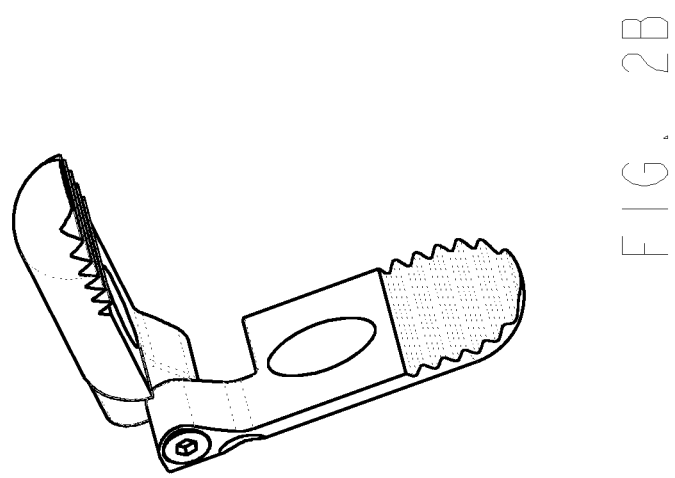
FIG. 2B is an assembled perspective view of the jaw assembly of FIG. 1A.
Figure 2A:
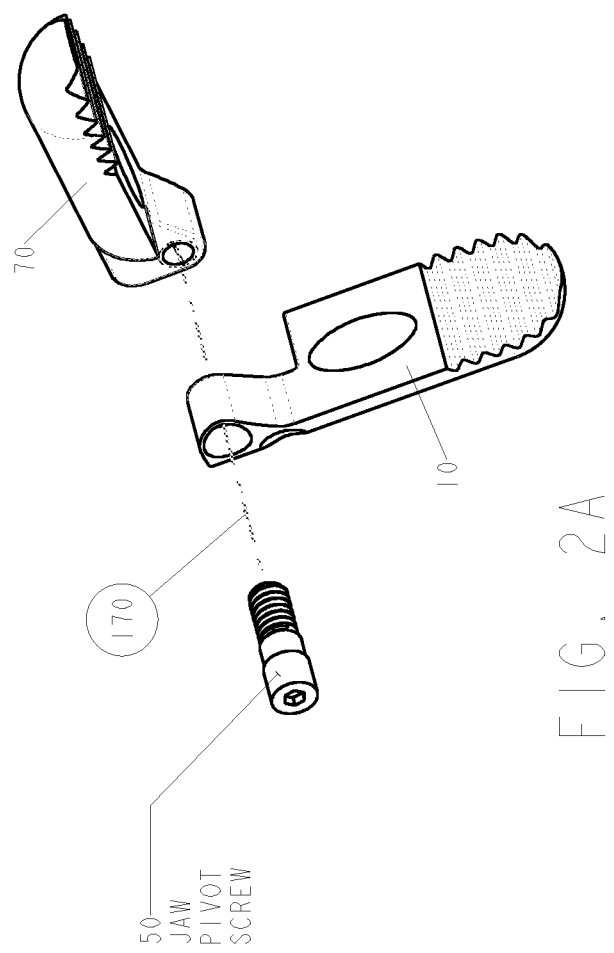
FIG. 2A is an exploded perspective view of components of the jaw assembly of FIG. 1A.

FIG. 2A is an exploded perspective view of components of the jaw assembly of FIG. 1A. FIG. 2B is an assembled perspective view of the jaw assembly of FIG. 1A. The jaws 70 and 10 are not symmetric. They are rotatably mounted to each other, so as to form an assembly, by jaw pivot screw 50, which passes through a hole formed in jaw 10 and is seated in jaw 70.

Figure 3A:
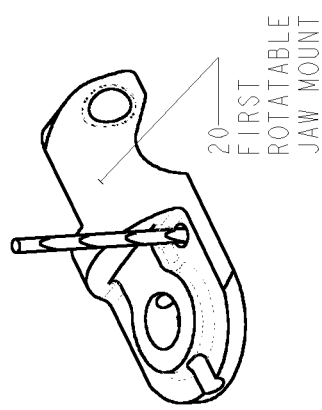
FIG. 3A is a side perspective view of the first rotatable jaw mount 20 of FIG. 1A, also showing the attached first cable 100.
Figure 3B:
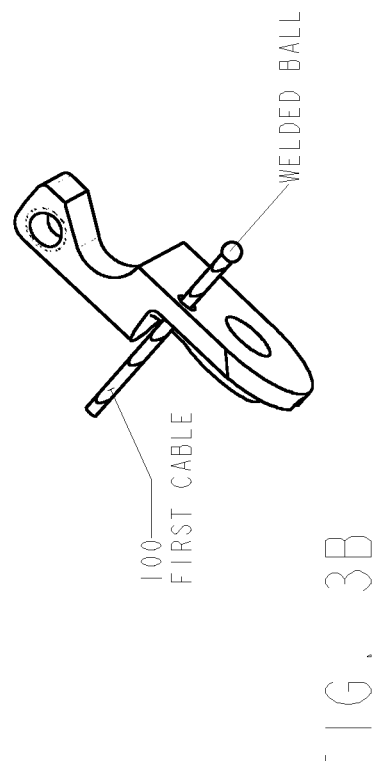
FIG. 3B is an edge perspective view of the first rotatable jaw mount 20 of FIG. 3A.

FIG. 3A is a side perspective view of the first rotatable jaw mount 20 of FIG. 1A, also showing the attached first cable 100. FIG. 3B is an edge perspective view of the first rotatable jaw mount 20 of FIG. 3A. The cable 100, at its distal end, passes through a hole in the first rotatable jaw mount 20 and is coupled to it by a welded ball that prevents exit of the cable from the hole. The cable 110 is similarly affixed to the second rotatable jaw mount 25.

Figure 4B:
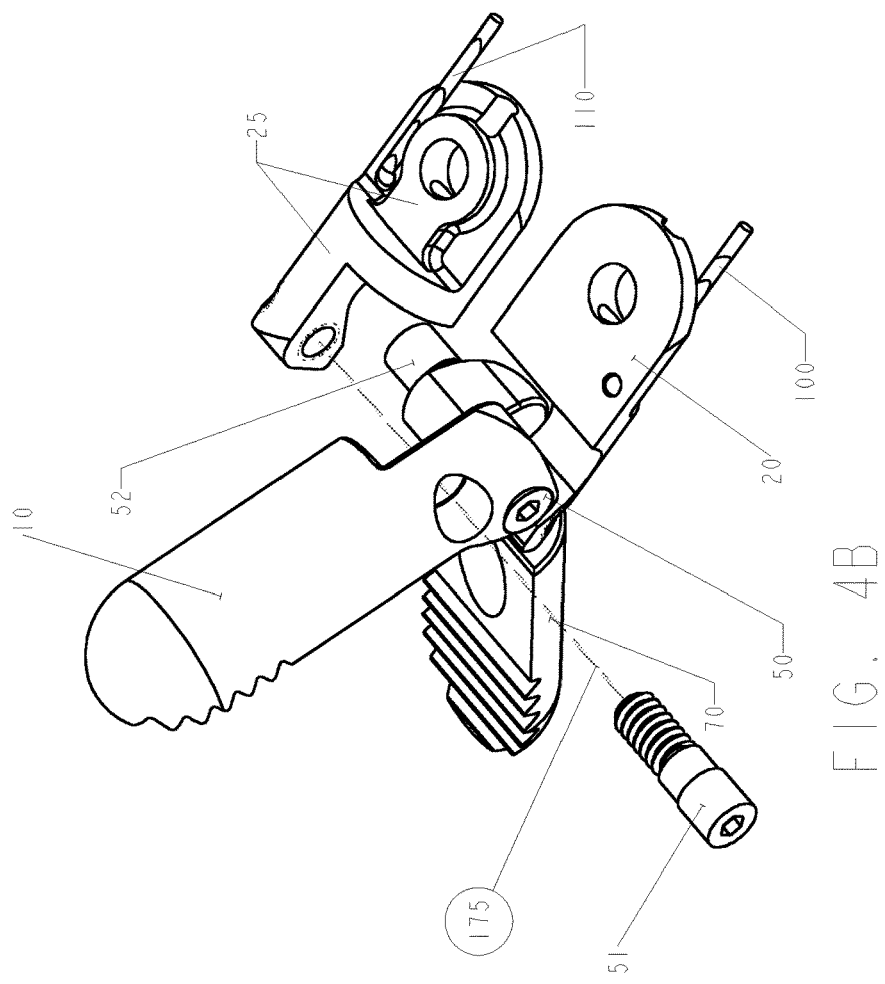
FIG. 4B is an exploded perspective view of the components of FIG. 4A.
Figure 4A:
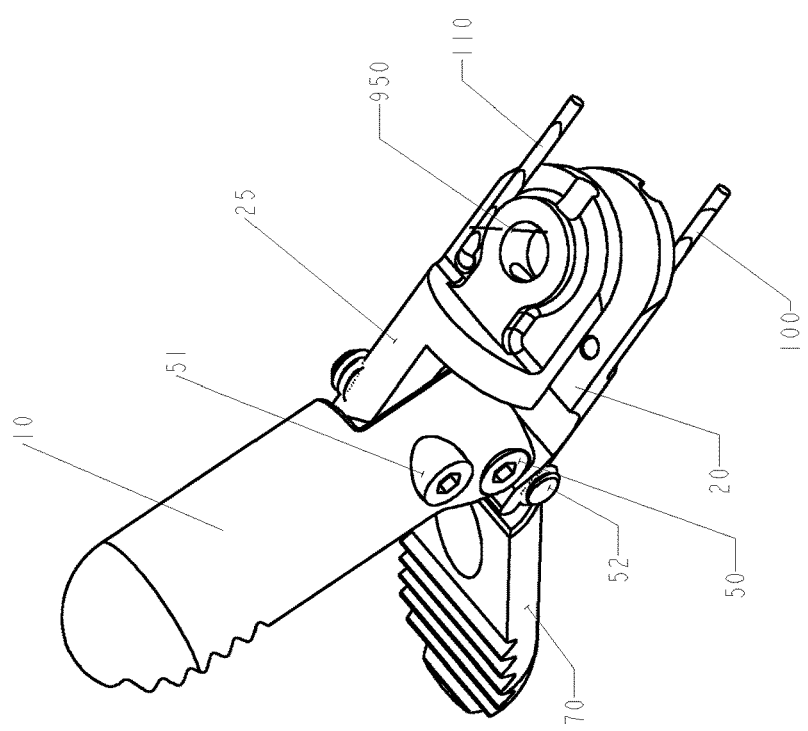
FIG. 4A is an assembled perspective view of components of FIG. 1A including the jaw assembly with the first and second rotatable jaw mounts 20 and 25 with corresponding first and second cables 100 and 110.

FIG. 4A is an assembled perspective view of components of FIG. 1A including the jaw assembly with the first and second rotatable jaw mounts 20 and 25 with corresponding first and second flexible cables 100 and 110. FIG. 4B is an exploded perspective view of the components of FIG. 4A. In FIG. 4A, it can be seen that, after the cable 110 emerges from the hole in the second rotatable jaw mount 25, it experiences a bend so as to follow a path, parallel to the longitudinal axis 200. Cable 100 experiences a similar bend and follows a similar path. However, a difference between orientation of cables 110 and 100 is that each one is coupled to its respective rotatable jaw mount on a different side of the yoke pivots 90 and 95. Consequently tension on cable 110 will cause clockwise motion of the jaw plane relative to the yoke pivots 90 and 95 as shown in FIG. 4A, whereas tension on cable 100 will cause counterclockwise motion of the jaw plane relative to the yoke pivots 90 and 95.

FIG. 13A is a top view of an embodiment of the present invention including components of FIGS. 1A and 1B as well as the proximal end of the device showing a housing in phantom and a spooling system for cables 100 and 110, in this view with the jaws closed and aligned with the longitudinal axis. FIG. 13B is a top view of the embodiment of FIG. 13A, in this view with the jaws closed and articulated at approximately a right angle to the longitudinal axis 200. In these figures, the first cable 100 is threaded under idler pulley 271, and over idler pulley 272, to capstan assembly 275, on which it is wound. Similarly, the second cable 110, is threaded over idler pulley 273, under idler pulley 274, to capstan assembly 270, on which it is wound.

As shown in FIG. 14B, the capstans are a component of the swivel assembly 260 and are inserted into the swivel assembly by means of a cylindrical protrusion on the base of the capstan and into a mounting hole located in the swivel assembly. The swivel assembly is moved angularly, in relation to the longitudinal axis 200, by the relative position of the pusher rods 131 shown in FIGS. 16A, 16B, 16C and 16D. The capstan assemblies 270 and 275 are either powered by an appropriate servo motor system or configured for manual operation. When the capstans are motorized, the swivel assembly 260 is locked into a neutral position, relative to the longitudinal axis 200, as shown in FIG. 14B. The capstans 275 and 270 are coupled to cables 100 and 110 respectively, and experience torque as a result of the cable coupling. The capstans have a series of circumferential detents to restrict rotation and lock the capstans in place. In a manual configuration, one cable is advanced by the change of the angle of the swivel assembly and the other cable is simultaneously and equally retracted. This motion controls pivoting of the jaw assembly.

FIG. 14A is a perspective view of the proximal end of the embodiment of FIGS. 13A and 13B, with the upper portion of the housing 255 removed. In this view can be seen the capstan assemblies 270 and 275, the first and second cables 100 and 110 respectively, the idler pulleys 271, 272, 273, and 274, the outer sheath 40, the pushrod 130, and the longitudinal axis 200. FIG. 14B is a similar perspective view of the embodiment of FIG. 14A, showing the swivel assembly 260, removed from the housing 255, in relation to the pushrod 130. The pushrod 130 is mounted in the housing 255 for axial translation, forward and back, of the entire distal assembly only and engages into the pin 132 of the case 801 as shown in FIG. 16C. The outer sheath 40 is coupled rigidly to the housing 255, and rotates when housing 255 is rotated. Housing 255 is rotated by the angular rotation of the rotation pins 131 and they in turn are controlled by a rotation mechanism either manually or motorized contained in case 801.

FIG. 14C is a view similar to that of FIG. 14B, but with capstan assemblies 270 and 275 exploded from their seated positions view of FIG. 14B showing how the locking pins 280 and 285 are engaged into the swivel assembly 260 and the capstans 270 and 275. The locking pins are used to prevent the capstans from rotating, thereby locking the cables 100 and 110 in position. In a motorized embodiment of the device, the capstans are motorized to allow the cables to move while the locking pins are no longer used and the swivel assembly 260 is locked in place.

Figure 15:
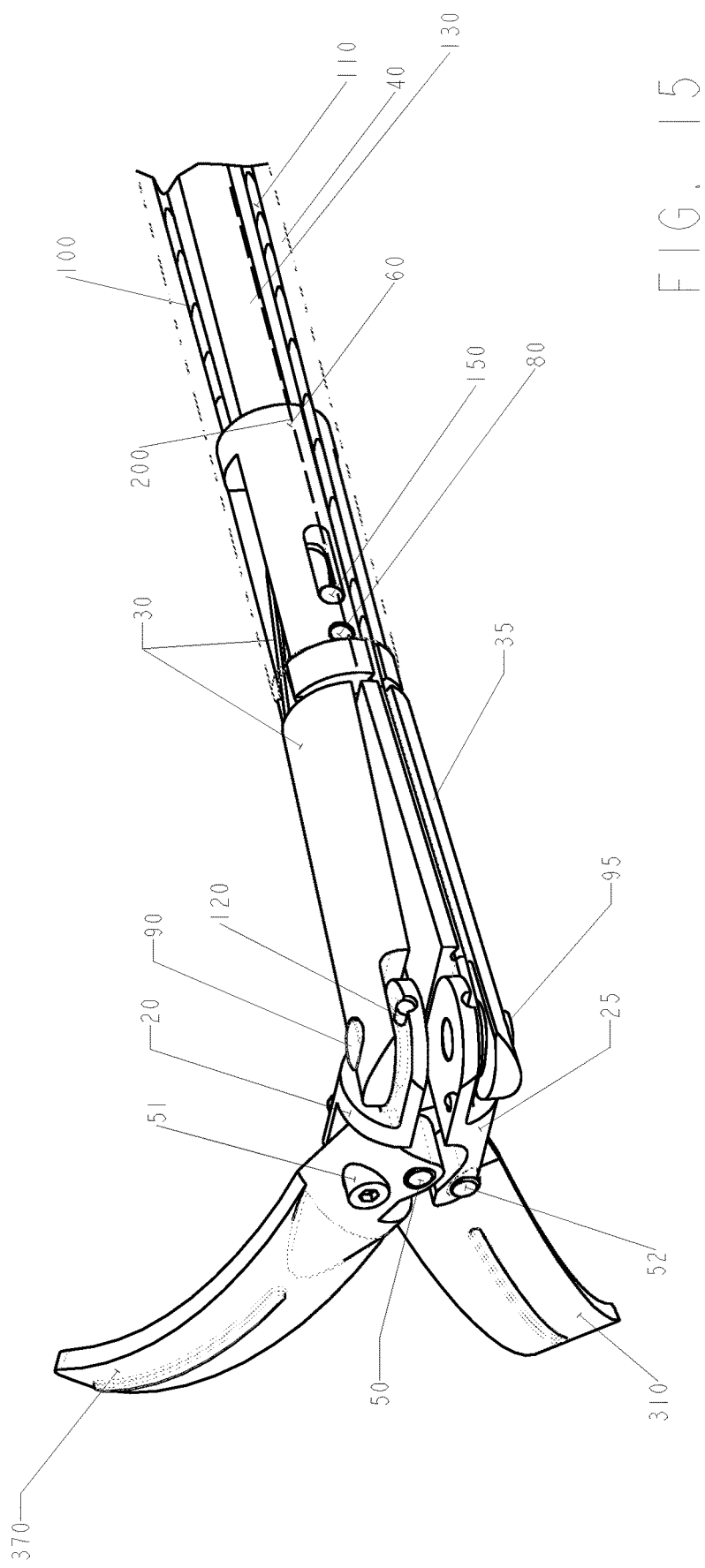
FIG. 15 is a perspective view of a distal end of a device, in accordance with an embodiment of the present invention, wherein the jaws are implemented as a pair of scissors in lieu of the grasping configuration of the preceding embodiment.

Although the jaws described thus far are shown as configured for grasping, they may be equally configured as scissor blades for cutting, as illustrated in FIG. 15, which is a perspective view of a distal end of a device, in accordance with an embodiment of the present invention, wherein the end effector is implemented as a pair of scissors 370 and 310 in lieu of the jaws of the preceding embodiment. The other items identified in FIG. 15 correspond to similar items in FIG. 1A.

FIGS. 16A, 16B, 16C, and 16D are top views of the end effector of FIG. 1A showing the entire disposable portion 800 of the instrument in relation to a portion 801 of the case, to which the disposable portion 800 is removably attachable. The portion 801 of the case includes a set of threads 802 configured to receive a nut (not shown) engaged against the disposable portion 800 so as to secure the two portions 800 and 801. When the disposable portion 800 is attached to the portion 801 of the case, the axially movable connecting rod 132 engages in the pushrod 130. The pushrod 130 includes a snap ring (not shown) that removably engages the connecting rod 132. (When the aforementioned nut is loosened, it drives the disposable portion 800 away from the case portion 801 so as to remove the connecting rod 132 from the snap ring of the pushrod 130.) When the pushrod 130 and the connecting rod 132 are engaged, then the connecting rod 132 can move the pushrod forward and backward to open and to close the end effector as described above. Also when the pushrod 130 and the connecting rod 132 are engaged, the axis rotation drivers 131 can interface with the disposable portion 800 to cause a change in the angle of the end effector. Also when the disposable portion 800 is attached to the portion 801 of the case, the resulting instrument has three degrees of freedom in operation: (1) opening and closing of the jaws (achieved by use of the pushrod 130), (2) adjustable articulation of the jaw plane relative to the longitudinal axis (achieved by use of the axis rotation drivers 131, cables 100 and 110, etc.), and (3) rotation of the jaw assembly about the longitudinal axis regardless of its articulation (achieved by rotating the entire instrument).

In FIG. 16A, the axis rotation drivers 131 are in a neutral position and detached from the disposable portion 800, and the end effectors face straight along the longitudinal axis 200.

In FIG. 16B, the axis rotation drivers 131 are engaged against the swivel 260; because the rotation pins are in a relatively neutral position, the distal assembly is facing straight ahead.

In FIG. 16C, the axis rotation drivers 131 are in a maximum deflected position and detached from the disposable portion 800. The end effectors are aligned with the longitudinal axis 200. The swivel 260 is in a neutral condition prior to the engagement of the case 801 with the disposable portion 800.

In FIG. 16D, after the case 801 is engaged with the disposable portion 800, the swivel is forced axially into position by the axis rotation drivers 131 to cause the jaw plane to lie at right angles to the longitudinal axis 200.

Optionally, the jaws are configured to carry current to enable use thereof in electrocautery.

In addition to implementations of the end effector for grasping and for cutting, in other implementations, the jaws can be configured for other applications, such as for stapling, for looping (wherein the jaws open and close a loop), etc.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. An end effector comprising:
an outer sleeve defining a central longitudinal axis;
first and second jaws;
a jaw pivot, mounted in each of the jaws, rotatably coupling the jaws and defining a jaw axis about which rotation of the jaws achieves opening and closing of the jaws, wherein (i) the jaw axis defines a jaw plane perpendicular thereto in which the jaws move relative to one another and (ii) the coupled jaws form a jaw assembly;
a split yoke assembly, generally aligned with the longitudinal axis, having first and second yoke segments, each yoke segment having a distal end and a proximal end, the yoke segments being mounted, about a scissors pivot, for scissors-movement with respect to one another;
a set of first and second rotatable jaw mounts, each jaw mount having proximal and distal ends, the distal end of each rotatable jaw mount being pivotally mounted, via a corresponding jaw mount pivot, to a corresponding one of the first and second jaws, and, the proximal ends of the first and second rotatable jaw mounts being pivotally mounted, via first and second yoke pivots, respectively, to the distal ends of the corresponding first and second yoke segments, wherein the jaw mount pivots define axes of rotation that are parallel to the jaw axis, to support opening and closing of the jaws in the jaw plane, and the first and second yoke pivots define first and second yoke pivot axes respectively and collectively configure rotation of the jaw assembly relative to the longitudinal axis so that, in a straight-ahead position of the jaw assembly about the jaw mount pivots, the jaw plane is aligned with the longitudinal axis, and in an angled position of the jaw assembly about the jaw mount pivots, the jaw plane is at an angle to the longitudinal axis;
first and second cables coupled at a distal end thereof to the set of rotatable jaw mounts and at a proximal end thereof to a jaw-positioning assembly configured to move the position of the jaw assembly between the straight-ahead position and the angled position;
a pushrod having proximal and distal ends, the pushrod being mounted in the outer sleeve for axial motion along the longitudinal axis between a forward position in a direction toward the jaw assembly and a rearward position in a direction away from the jaw assembly;

a linkage system, coupled (a) to the first and second yoke segments near the proximal ends thereof and (b) to the distal end of the pushrod, the linkage system configured to move the proximal ends of the yoke segments towards each other, and therefore the distal ends of the yoke segments away from each other, so as to cause the jaws to move into an open position, when the pushrod is in a first one of the forward and rearward positions, and to move the proximal ends of the yoke segments away from each other, and therefore the distal ends of the yoke segments toward each other, so as to cause the jaws to move into a closed position, when the pushrod is in a second one of the forward and rearward positions.

2. An end effector according to claim 1, wherein the proximal ends of the yoke segments have facing flattened surfaces that are approximately in the jaw plane when the jaw assembly is in the straight-ahead position, and the linkage system includes:

a set of angled slots formed in the proximal ends of the yoke segments, a yoke segment positioning system disposed around the proximal ends of the yoke segments and coupled to the outer sheath, and a positioning pin, mounted in the positioning system at right angles to the flattened surfaces of the proximal ends of the yoke segments, and located within the slots of both of the yoke segments, and the pushrod is coupled to the positioning pin, so that axial motion of the pushrod causes the positioning pin in combination with the angled slots to move the proximal ends of the yolk segments towards or away from each other, depending on the direction of the axial motion.

3. An end effector according to claim 1, further comprising first and second rocker pivot pins mounting the first and second rotatable jaw mounts to the first and second yoke pivots respectively, the first and second rocker pivot pins having axes perpendicular respectively to the first and second yoke pivot axes, and configured to allow relative motion of the first and second rotatable jaw mounts about the yoke rocker pivot pins that is required when the jaws are open and at an angle to the longitudinal axis.

4. An end effector according to claim 1, wherein the first and second rotatable jaw mounts are made of resilient deformable material configured to allow relative motion of the first and second rotatable jaw mounts about the yoke rocker pivot pins that is required when the jaws are open and at an angle to the longitudinal axis.

5. An end effector according to claim 1, wherein the jaws are configured for grasping.

6. An end effector according to claim 2, wherein the jaws are configured for grasping.

7. An end effector according to claim 1, wherein the jaws are configured as scissor blades for cutting.

8. An end effector according to claim 2, wherein the jaws are configured as scissor blades for cutting.

9. An end effector according to claim 1, wherein the jaws are configured to carry current to enable use thereof in electrocautery.

10. An end effector according to claim 1, wherein the jaws are configured to open and close a loop.

\* \* \* \* \*

UNITED STATES PATENT AND TRADEMARK OFFICE
CERTIFICATE OF CORRECTION

PATENT NO. : 10,709,517 B2  
APPLICATION NO. : 15/872288  
DATED : July 14, 2020  
INVENTOR(S) : Gerald J. Berkelaar Page 1 of 1

It is certified that error appears in the above-identified patent and that said Letters Patent is hereby corrected as shown below:

In the Claims

In Column 12, Line 2:  
Replace "yolk"  
With --yoke--

Signed and Sealed this  
Twenty-second Day of September, 2020

Andrei Iancu  
*Director of the United States Patent and Trademark Office*